United States Patent [19]
Rogers et al.

[11] 4,135,151
[45] Jan. 16, 1979

[54] APPARATUS FOR DETECTING WET AND ICY SURFACE CONDITIONS

[75] Inventors: John O. Rogers; Robert O. Gregory, both of St. Louis County, Mo.

[73] Assignee: Surface Systems, Inc., St. Louis County, Mo.

[21] Appl. No.: 860,292

[22] Filed: Dec. 14, 1977

[51] Int. Cl.² ............................................. G01R 27/26
[52] U.S. Cl. ............................................. 324/61 R
[58] Field of Search ................. 324/61 R, 61 P, 65 R, 324/57 R; 328/4; 361/280

[56] References Cited

U.S. PATENT DOCUMENTS

| 3,428,890 | 2/1969 | Peck et al. | 324/61 R |
| 3,873,927 | 3/1975 | Overall | 324/61 R X |
| 3,882,381 | 5/1975 | Gregory | 324/61 R |
| 3,986,110 | 10/1976 | Overall | 324/61 R |

Primary Examiner—Stanley T. Krawczewicz
Attorney, Agent, or Firm—Koenig, Senniger, Powers and Leavitt

[57] ABSTRACT

Apparatus for detecting wet and icy conditions on the surface of a pathway. A block of electrically insulative material is embedded in a pathway with the top surface of the block being substantially flush with the surface of the pathway and exposed to atmospheric precipitation. A sensor electrode is positioned a predetermined distance beneath the top surface of the block and encapsulated in the block so that the accumulation of atmospheric precipitation on the top surface of the block affects the capacitance and conductance between the sensor electrode and the pathway. A time-varying electrical current having an amplitude which is substantially constant and independent of the accumulation of atmospheric precipitation on the top surface of the block is supplied to the sensor electrode. The apparatus also includes an amplifier for amplifying an electrical signal applied to a pair of input terminals thereof. One input terminal of the amplifier is commonly connected to the source of the time-varying electrical current and to the pathway in the vicinity of the sensor electrode. The sensor electrode is connected to the other input terminal of the amplifier to complete a circuit between the source of the time-varying electrical current, the sensor electrode and the amplifier, thereby applying an electrical signal to the amplifier. The amplitude of the electrical signal at the input terminals of the amplifier is substantially solely a function of the change in capacitance and conductance between the sensor electrode and the pathway as atmospheric precipitation accumulates on the top surface of the block. An amplified signal from the amplifier is supplied to a precipitation signal circuit which in response to the amplitude of the amplified signal reaching a predetermined magnitude provides an output signal indicative of the presence of atmospheric precipitation on the pathway.

17 Claims, 4 Drawing Figures

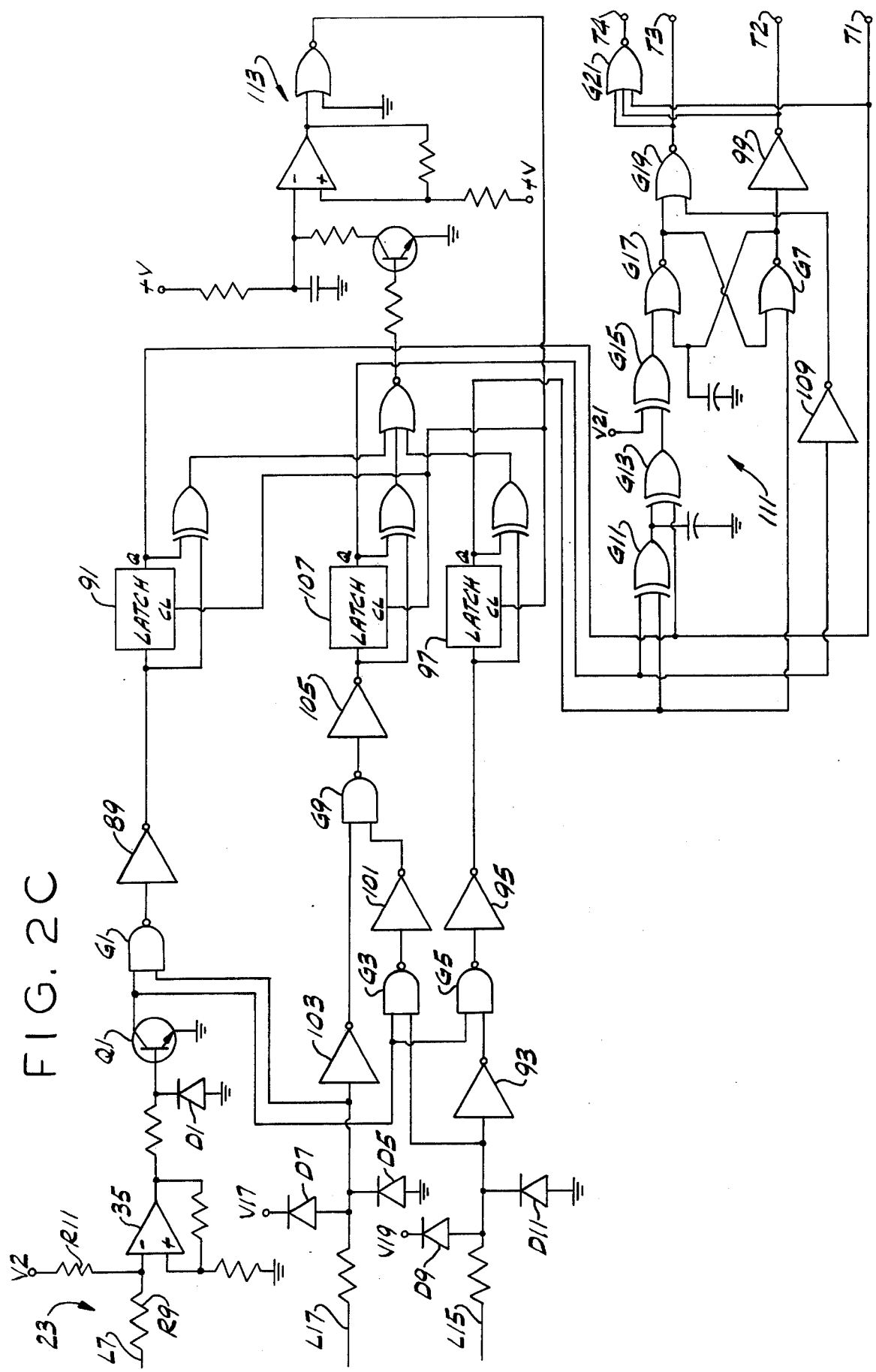

APPARATUS FOR DETECTING WET AND ICY SURFACE CONDITIONS

BACKGROUND OF THE INVENTION

This invention relates to precipitation detectors and particularly to apparatus for detecting wet and icy conditions on the surface of a pathway, such as highway or airport runway.

Such apparatus which detects wet and icy surface conditions is of tremendous aid to motorists, highway departments, airport managers, pilots and the like. A motorist can be made aware of an icy condition on a bridge deck before crossing it and take the necessary precautions. Likewise, once an airport manager is aware of an icy condition on one or more of his runways, he can divert planes to a non-icy runway or initiate deicing procedures on the affected runways. Motorists can be warned of a light accumulation of water on a dirty highway which is a hazard almost as well known as it is difficult to see.

A number of systems have been suggested for detecting precipitation on a pathway, such as those disclosed in coassigned U.S. Pat. Nos. 3,873,927 and 3,882,381, in U.S. Pat. Nos. 2,419,266, 3,243,793, and 3,428,890, and in French Pat. No. 2,078,982.

While prior art systems in general provide useful information on surface conditions it would be highly advantageous if their effectiveness could be improved in certain respects. Where the sensor is positioned in the most desirable location to accurately sense the actual surface conditions, viz., embedded in the pathway with its top surface generally coplanar with that of the pathway, it is exposed to the traffic such as passing cars and trucks and landing aircraft, etc. A sensor unit which has capacitor plates disposed a short distance, e.g., 1/16 inch (0.16 cm.) below the top surface of an epoxy encapsulated sensor is therefore subjected to considerable wear and abrasion. Thus the relatively thin layer of epoxy tends to be worn away subjecting the capacitor plates to damage and rendering the sensor unit inoperative.

If, however, the wear resistance and useful life of the sensor is improved by increasing the thickness of the overlying synthetic resin used for encapsulation, the sensitivity and reliability of the unit to surface precipitation is markedly diminished. Moreover, the response of prior art systems is frequently subject to drift and variation as a function of temperature. These are not easily compensable and result in possible inaccuracy and imprecision in indicating the actual surface conditions.

Where the system uses a signal generator in conjunction with a sensor, it is desirable that this generator and its associated components be located at a remote position, such as under the bridge or a considerable distance from the runway or highway surface where the sensor is embedded. However, to improve the sensitivity of such systems, higher frequency (e.g., 200 KHz) generators have frequently been used and this severely limits the distance the signal can be conducted by the usual wiring cable.

SUMMARY OF THE INVENTION

Among the several objects of the present invention may be noted the provision of an apparatus which reliably detects wet and icy conditions on the surface of a pathway and which is sufficiently sensitive to accurately detect the presence of precipitation on a pathway; the provision of such apparatus in which the sensor has greatly improved resistance to wear and abrasion and also has enhanced sensitivity; the provision of such apparatus which accurately and reliably detects the presence of precipitation on a pathway over wide variations in ambient temperature; and the provision of such apparatus which allows improved design flexibility in the placement of the various parts of the apparatus. Other objects and features will be in part apparent and in part pointed out hereinafter.

Briefly, apparatus of the present invention comprises a block of electrically insulative material adapted to be embedded in a pathway with the top surface of the block substantially flush with the surface thereof and exposed to atmospheric precipitation, the nature of which is to be detected. A sensor electrode is encapsulated in the block and is positioned a predetermined distance beneath the top surface of the block so that the accumulation of atmospheric precipitation on the top surface affects the capacitance and conductance between the electrode and the pathway. The apparatus also includes a current generator for supplying to the sensor electrode a time-varying electrical current having an amplitude which is substantially constant and is independent of the accumulation of atmospheric precipitation on the top surface of the block. An amplifier for amplifying an electrical signal applied to a pair of input terminals thereof is commonly connected, by way of one of the input terminals, to the time-varying electrical current generator and to the pathway in the vicinity of the sensor electrode. The sensor electrode is connected to the other input terminal of the amplifier to complete a circuit between the time-varying electrical current generator, the sensor electrode and the amplifier thereby to apply an electrical signal to the amplifier. The amplitude of the electrical signal at the input terminals of the amplifier is substantially solely a function of the change in capacitance and conductance between the sensor electrode and the pathway as atmospheric precipitation accumulates on the top surface of the block. The apparatus also comprises precipitation signal means responsive to the amplitude of an amplified electrical signal from the amplifier reaching a predetermined magnitude for providing an output signal indicative of the presence of atmospheric precipitation on the pathway.

BRIEF DESCRIPTION OF THE DRAWINGS

FIGS. 2A–2C are schematics of the electrical circuitry used with the sensing apparatus shown in FIG. 1.

Corresponding reference characters indicate corresponding parts throughout the several views of the drawings.

DESCRIPTION OF A PREFERRED EMBODIMENT

Figure 1:
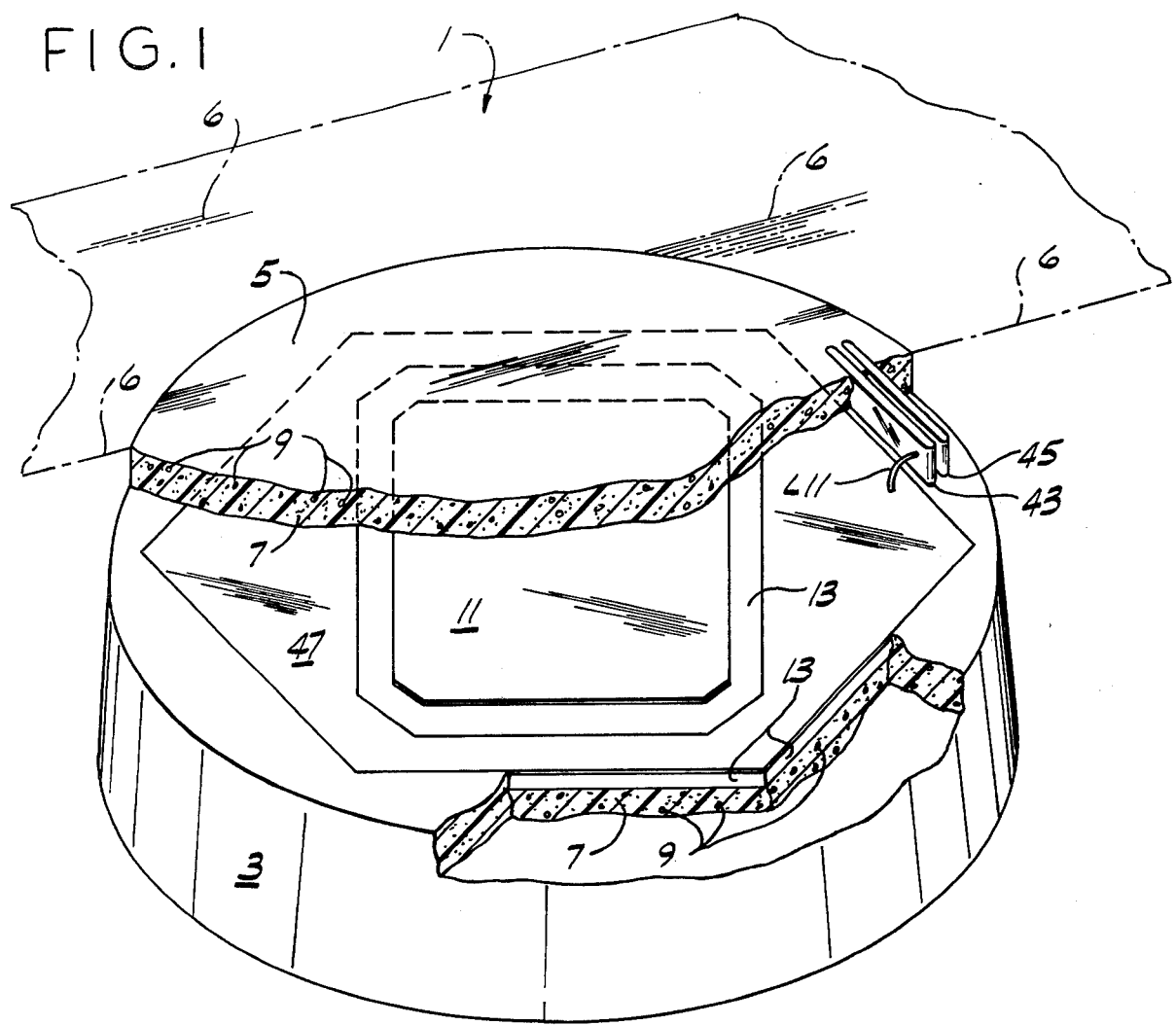
FIG. 1 is a perspective view of sensing apparatus of the present invention with certain parts broken away for clarity.

Referring now to the drawings, apparatus of this invention for detecting wet and icy conditions on the surface of a pathway includes a sensor indicated generally at 1. Sensor 1 includes a block 3 of electrically insulative material having a flat top surface 5. Block 3 is embedded in a pathway, such as an airport runway or the surface of a bridge, with its top surface 5 being positioned so it is substantially flush with the surface of the pathway. In this position top surface 5 is exposed to the atmospheric precipitation, i.e., rain, sleet, snow, etc., which falls on the surrounding pathway. A typical pathway is indicated by phantom lines 6 in FIG. 1. The electrically insulative material making up block 3 includes a thermosetting synthetic resin material 7 having a dielectric constant which is relatively independent of temperature. An excellent resin material 7, generally known as an epoxy resin, is obtained using diglycidyl ether of Bisphenol A with triethylenetetramine hardener. For dimensional stability, it is preferred that the electrically insulative material making up block 3 further include an inert filler material, indicated generally at 9, having a dielectric constant substantially equal to that of resin material 7. Excellent results have been obtained using clean, dry 1/16 inch silica glass beads or clean silica sand as inert filler material 9. The proportion of resin material 7 to filler material 9 is, for example, 50:50 by weight.

A large, roughly square sensor electrode 11 is encapsulated in block 3 and positioned a predetermined distance, on the order of one-quarter inch, beneath top surface 5 of block 3. Electrode 11 is a metallic foil material bonded to the top surface on a substrate material 13, typically an insulating board suitable for use in making printed circuit boards, which is itself encapsulated in block 3. The capacitance and conductance between electrode 11 and pathway 6 is represented in phantom on FIG. 2A by equivalent capacitors C1 and C3 and equivalent resistor G1. Discrete components having the values of capacitors C1 and C3 and resistor G1 are not actually present in the circuit but the capacitive and conductive effects between sensor electrode 11 and the pathway, i.e., ground, are the equivalent of having resistor G1 and capacitors C1 and C3 in the circuit. Hereinafter the circuit will be described as if resistor G1 and capacitors C1 and C3 were discrete components. Capacitor C1 represents the capacity between sensor electrode 11 and top surface 5 of block 3, while capacitor C3 and resistor G1 represent the capacity and conductance between top surface 5 and pathway 6. Pathway 6 is, of course, by definition at ground potential and can be considered as an extremely large plate at ground potential extending from the sensor block in all directions.

A constant-voltage oscillator 15 and a 200 pF capacitor C5 constitute means for supplying to sensor electrode 11 a time-varying electrical current 16 having an amplitude which is substantially constant and is independent of any accumulation of atmospheric precipitation on top surface 5 of block 3. Oscillator 15 produces a sine wave signal at a frequency of approximately 5 KHz and supplies this signal to a resistor R1 and a thermistor T1. These temperature compensating components are necessary to compensate for a small change in the capacitance of capacitor C1 caused by a change in the dielectric constant of materials 7 and 9 of block 3 with temperature, and together constitute means connected to oscillator 15 and sensor electrode 11 for compensating for temperature-induced changes in the dielectric constant of the insulative material making up block 3.

Oscillator 15 may be placed up to 500 feet from sensor electrode 11 because of the relatively low frequency being generated.

Some of current 16 applied to sensor electrode 11 is lost, i.e., shunted to ground, due to capacitive and conductive effects between electrode 11 and pathway 6, the amount lost being a function of whether there is atmospheric precipitation on top surface 5. The capacitance between top surface 5 and pathway 6, represented by capacitor C3, is quite small when top surface 5 is dry and the conductance, represented by resistor G1, is virtually zero, resulting in practically no loss of current 16 from electrode 11 to pathway 6 in dry weather. When there is precipitation on surface 5, however, surface 5 is connected capacitively, conductively, or both to pathway 6 via the precipitation and the interface of that precipitatiion with the pathway causing a substantial loss of current 16 from electrode 11 to pathway 6.

Sensor electrode 11 is connected by means of a resistor R3 and a line L1 to the noninverting input terminal of an amplifier 17. A one meg resistor R5 is connected between line L1 and pathway 6 and provides a direct current bias path required by the amplifier input. The inverting terminal of amplifier 17 is connected by means of a line L3 to pathway 6, i.e., to ground. Likewise, oscillator 15 is connected by a line L5 to pathway 6. Of course, the actual ground connector of the circuit need not necessarily be inserted into pathway 6 itself since the potential of pathway 6 and any other suitable earth ground will be the same. Line L1 and resistor R3, therefore, complete a circuit between oscillator 15, sensor electrode 11 and amplifier 17. As a result, a time-varying electrical signal, designated by the reference numeral 19, is applied to the noninverting input of amplifier 17. Because of the current losses occurring from sensor electrode 11 to pathway 6, which reduce the amplitude of signal 19, the amplitude of this signal at the input terminals of amplifier 17 is substantially solely a function of the change in the capacitance and conductance between sensor electrode 11 and pathway 6 as atmospheric precipitation accumulates on top surface 5 of block 3. The output of amplifier 17 is, therefore, an amplified signal 21, the magnitude of which decreases as the capacitance between electrode 11 and pathway 6 increases, i.e., as atmospheric precipitation accumulates on surface 5 of block 3.

Amplified electrical signal 21 is supplied to a precipitation signal circuit, indicated generally at 23, which includes a voltage follower 25, a rectifying circuit indicated generally at 27, an inverting amplifier 29, a low-pass filter 31 consisting of a resistor R7 and a capacitor C7, a summing amplifier 33, a Schmitt trigger 35, and an n-p-n transistor Q1. Amplified signal 21 is rectified by rectifying circuit 27 and the harmonic components of the resulting signal are filtered out by low-pass filter 31, leaving only the average component of signal 21. This average component of signal 21 is supplied to a summing junction 37 of summing amplifier 33.

A balancing circuit, indicated generally at 39, also supplies a signal to summing junction 37. Balancing circuit 39 includes a negative twelve-volt source V1 and a potentiometer 41 which is adjusted so that the voltage at summing junction 37 is approximately zero when there is no precipitation on top surface 5 of block 3. Of course, when there is precipitation on surface 5, the magnitude of the average component of signal 21 is smaller than when there is no precipitation. This decreases the voltage at summing junction 37, causing it to be negative, and causing the output of summing amplifier 33 to be more positive. For example, the output of amplifier 33 is 0.5 V. or less when top surface 5 is "dry" and 2.0 V. or more when it is "wet". The output of summing amplifier 33 is supplied on a line L7 to a voltage divider consisting of a resistor R9, a resistor R11 and a negative twelve-volt source V2. The values of resistors R9 and R11 are chosen to ensure that Schmitt trigger 35, whose input is connected to the voltage divider between these two resistors, will have a negative output when the output of summing amplifier 33 is 2.0 v. or more, and will have a positive output if the output of summing amplifier 33 is 0.5 V. or less. The output of Schmitt trigger 35 is supplied to the base of transistor Q1. Negative voltage excursions at the base of transistor Q1 are prevented by a clamping diode D1. The collector of transistor Q1 is connected to a TTL NAND gate G1. If the output of Schmitt trigger 35 is negative, i.e., there is precipitation on pathway 6, transistor Q1 will not conduct and the voltage measured at the collector of transistor Q1 will be about 5.0 volts. This voltage on the collector is an output signal of precipitation signal circuit 23 indicative of the presence of atmospheric precipitation on pathway 6. If the output of Schmitt trigger 35 is positive, i.e., the surface of pathway 6 is clear, transistor Q1 conducts and the voltage measured at the collector will be around zero volts. This state of transistor Q1 is considered to be the absence of an output signal from precipitation signal circuit 23. The exact triggering point of Schmitt trigger 35 relative to the amplitude of amplified signal 21 is, of course, a function of the values of the components making up precipitation signal circuit 23. It is only when the amplitude of amplified electrical signal 21 reaches, i.e., falls to, a predetermined magnitude, determined by the values of the components of precipitation circuit 23, that the output of Schmitt trigger 35 goes negative which provides the output indicative of precipitation at the collector of transistor Q1. The values of these components are adjusted to provide an accurate indication of precipitation on top surface 5 of block 3 and to reduce or eliminate false readings. Particularly where the predetermined magnitude of amplified signal 21 corresponds to a summing amplifier 33 output of at least two volts, excellent results are obtained. Thus, it can be seen that precipitation signal circuit 23 constitutes means responsive to the amplitude of amplified electrical signal 21 from amplifier 17 reaching a predetermined magnitude for providing an output signal, i.e., the five-volt output signal measured at the collector of transistor Q1, indicative of the presence of atmospheric precipitation on pathway 6. In particular, precipitation signal circuit 23 constitutes such means which are responsive to the amplitude of amplified electrical signal 21 falling to the predetermined magnitude.

Referring now to FIG. 1, two parallel plates, designated by the reference numerals 43 and 45, are embedded in block 3 with their top surfaces flush with top surface 5, forming a pair of spaced electrodes exposed to atmospheric precipitation. As is clearly seen from FIG. 2A, electrode 43 is commonly connected by a line L9 to ground, i.e., as explained above, to pathway 6. That is, line L9 constitutes means for commonly connecting electrode 43 and pathway 6.

Electrode 43 has a double function. In conjunction with electrode 45 it acts as an ice sensor, as is explained below. But it also serves to enhance the electrical connection between pathway 6 and atmospheric precipitation on top surface 5 of sensor block 3, since it is in physical contact with the precipitation on surface 5 as well as being electrically connected by line L9 to pathway 6. Of course, such enhancement electrodes could be of a wide variety of shapes and sizes.

Referring again to FIG. 1, there is a further electrode, designated by the reference numeral 47, encapsulated in sensor block 3. Electrode 47 is spaced from sensor electrode 11, is coplanar thereto, and substantially surrounds sensor electrode 11 in their mutual plane. Electrode 47 is connected to pathway 6 by a line L11 between it and electrode 43, which is itself connected to pathway 6. Line L11, of course, constitutes means for commonly connecting electrode 43 and electrode 47. Of course, many means other than line L11 and electrode 43 could be used to connect pathway 6 and electrode 47; all that is required is that electrode 47 be in electrical contact with the ground of the system. Of course electrode 47 could be omitted without changing the method of operation of the present apparatus.

Figure 2B:
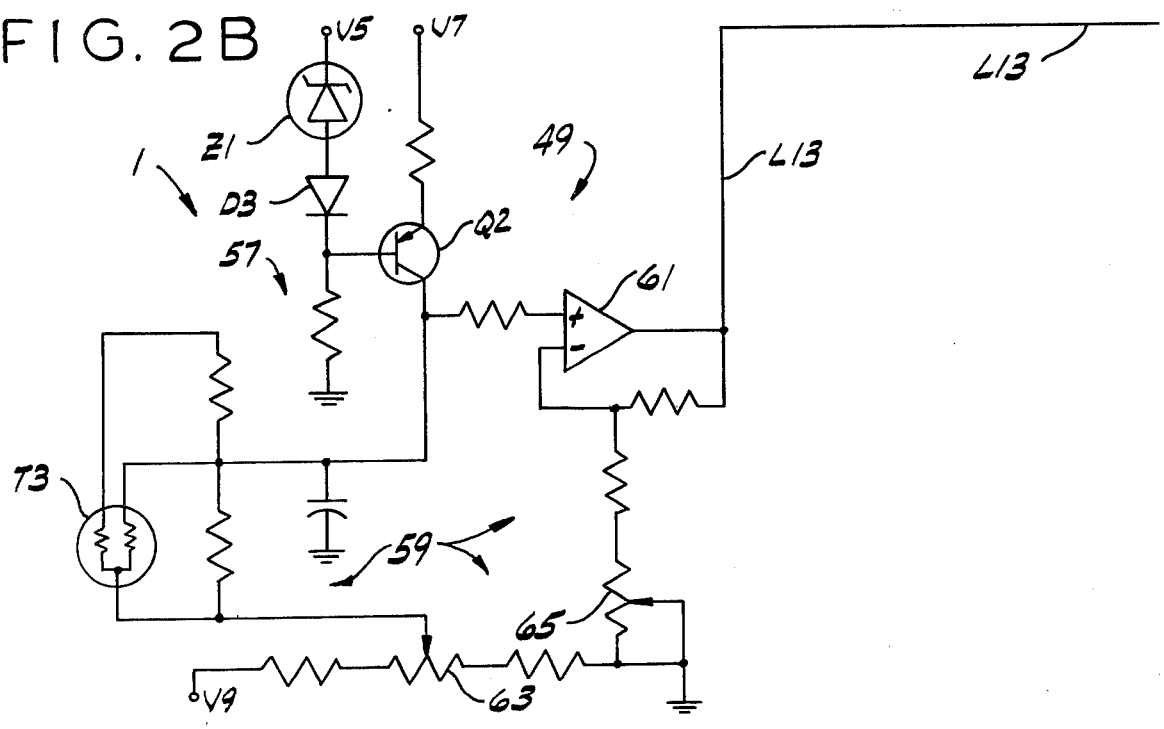
Figure 2A:
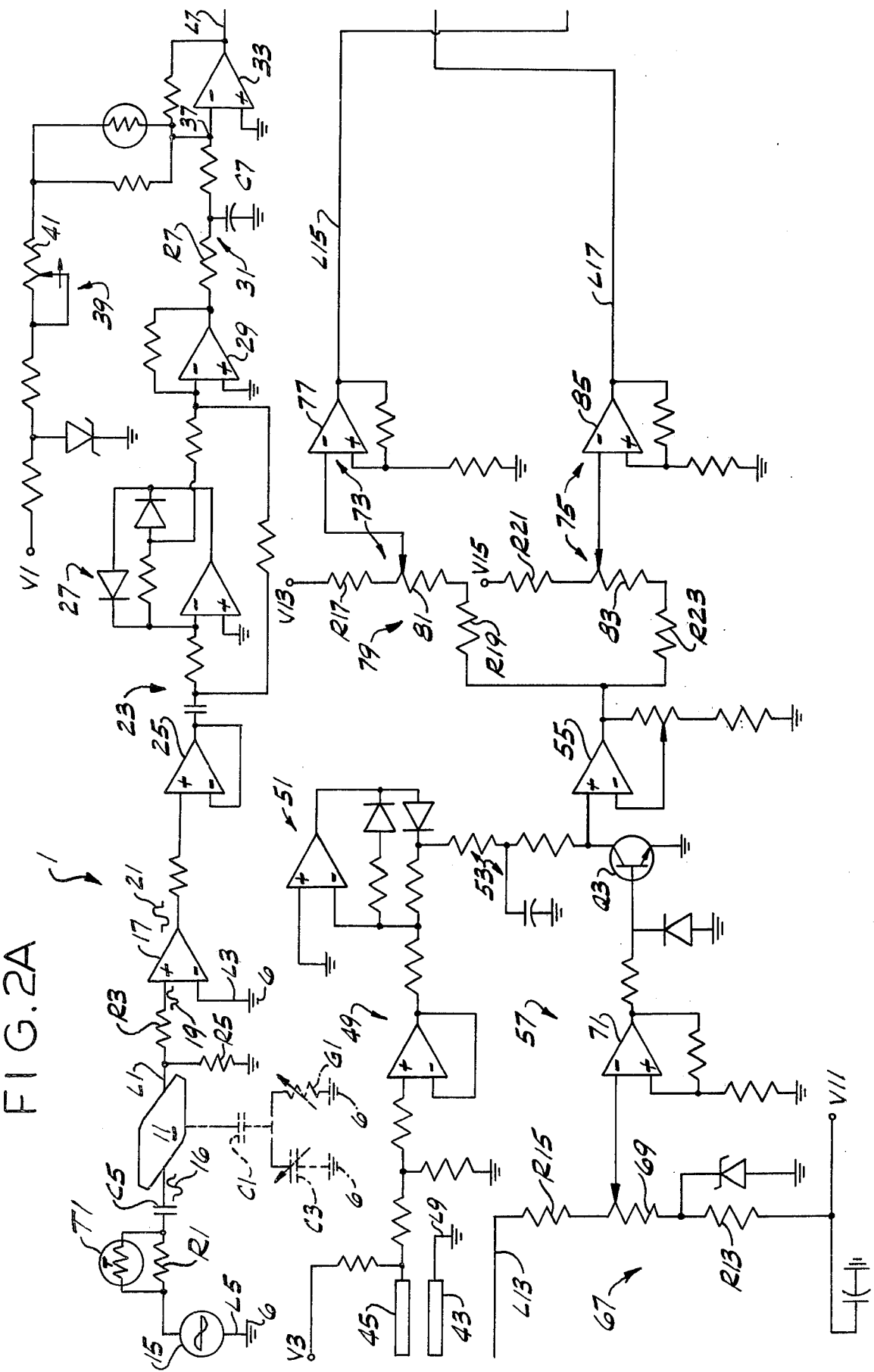

Referring now to FIG. 2A, electrode 45 is connected to a twelve-volt alternating current source V3 and is also connected to a state indicator circuit indicated generally at 49. State indicator circuit 49 constitutes means for supplying an output signal the magnitude of which is a function of the resistance between electrodes 43 and 45. Since electrodes 43 and 45 are exposed to atmospheric precipitation, the resistance between them is affected by that precipitation, and in particular the resistance between them is greater when the precipitation is ice than when it is water. As the resistance increases between electrodes 43 and 45, less current is lost or shunted from electrode 45 to electrode 43 and, therefore, the magnitude of the signal supplied from voltage source V3 to state indicator circuit 49 increases. Of course, the magnitude of the signal supplied to state indicator circuit 49 will vary as a function of the relative amounts of ice and water between electrodes 43 and 45. Briefly, state indicator circuit 49 rectifies this signal in a rectifier circuit indicated generally at 51, filters out the harmonic components of the rectified signal in a low-pass filter indicated generally at 53, and amplifies the resulting average component of the signal in an amplifier 55, the magnitude of the output signal of which, therefore, varies as a function of the resistance between electrodes 43 and 45. If there is ice between electrodes 43 and 45, the output of amplifier 55 is, for example, 0.9 volts or more, 0.9 volts being an exemplary predetermined ice threshold magnitude. If only water is between the sensors, the output of amplifier 55 is less than 0.75 volts, 0.75 volts being a predetermined alert threshold magnitude. The predetermined thresholds set out above are the preferred thresholds when salt is spread on pathway 6 to retard icing. If other anti-icing agents, such as ethylene glycol and urea are used on pathway 6, the predetermined thresholds will differ from those set out above. The thresholds of the apparatus used in any particular pathway 6 are, of course, set to correspond to the anti-icing agent typically used on that pathway.

If the temperature of pathway 6 is greater than a predetermined temperature, e.g., 33° F. (0.56° C.), above which ice will not form, the output of amplifier 55 should be less than the predetermined alert threshold magnitude, e.g., 0.75 volts. To ensure that this is the case, state indicator circuit 49 includes a temperature measuring circuit, indicated generally at 57 (FIG. 2B). Temperature measuring circuit 57 includes two twelve-volt sources V5 and V7. Voltage source V5 is connected through a Zener diode Z1 and a diode D3 to the base of a p-n-p transistor Q2, while voltage source V7 is connected to the emitter of transistor Q2, causing it to supply current to a resistor network indicated generally at 59, which includes a thermistor T3. Also connected to resistor network 59 is a negative twelve-volt source V9. The collector of transistor Q2 is connected to the noninverting input of an amplifier 61. The voltage measured at the collector of transistor Q2 is a function of the resistance of thermistor T3. Since thermistor T3 has a negative temperature coefficient of resistance, the output of amplifier 61 varies inversely with temperature. The magnitude of the output of amplifier 61 can, of course, be adjusted as desired by means of two potentiometers 63 and 65 which make up part of resistor network 59.

The output of amplifier 61 is supplied on a line L13 to a voltage divider, indicated generally at 67, which includes a twelve-volt source V11, a resistor R13, a potentiometer 69, and a resistor R15. The slider terminal of potentiometer 69 is connected to the input of a Schmitt trigger 71. When the temperature of pathway 6 reaches 33° F. (0.56° C.), the output of amplifier 61 is such that the input voltage to Schmitt trigger 71 is negative, causing its output voltage to be positive. This positive voltage is supplied to the base of an n-p-n transistor Q3, causing it to conduct. The collector of transistor Q3 is connected to the noninverting input of amplifier 55, so that when transistor Q3 conducts, that input becomes practically zero, ensuring that the output of amplifier 55 is less than 0.75 volts, i.e., ensuring that said amplifier does not cause an (erroneous) indication that ice is present between electrodes 43 and 45 when the temperature is above 33° F. (0.56° C.).

The output of amplifier 55 is supplied to an ice indicator circuit, indicated generally at 73, which provides an output indicative of the fact that the output of amplifier 55 is above the predetermined ice threshold magnitude, i.e., 0.9 volts, and to an alert circuit, indicated generally at 75, which provides an output indicative of the fact that the output of amplifier 55 is above the predetermined alert threshold magnitude, i.e., 0.75 volts. Ice indicator circuit 73 includes a negative twelve-volt source V13, a Schmitt trigger 77, and a voltage divider 79 consisting of a resistor R17, a potentiometer 81 and a resistor R19. The input to Schmitt trigger 77 is connected to the slider terminal of potentiometer 81. Potentiometer 81 is set so that the input voltage to Schmitt trigger 77 is greater than the trigger voltage when the output of amplifier 55 is 0.9 volts or more. Thus, an output of amplifier 55 which indicates ice between electrodes 43 and 45 causes the output of Schmitt trigger 77 to be negative, while an amplifier 55 output of less than 0.9 volts causes the output of Schmitt trigger 77 to be positive.

Alert indicator circuit 75 includes a negative twelve-volt source V15, a resistor R21, a potentiometer 83, a Schmitt trigger 85 connected thereto, and a resistor R23. Alert indicator circuit 75 differs from ice indicator circuit 73 in the values of the resistors, however, since Schmitt trigger 85 has a negative output whenever the alert threshold magnitude, i.e., 0.75 volts, has been reached or surpassed.

The outputs of Schmitt triggers 77 and 85 are supplied on lines designated by the reference characters L15 and L17 to an electrical logic circuit indicated generally at 87 on FIG. 2C. Logic circuit 87 uses these two outputs, indicative of ice and slush respectively, together with the voltage on the collector of transistor Q1, which indicates the presence of any precipitation on surface 5 of block 3, to provide four mutually exclusive outputs indicating a wet surface condition, an icy surface condition, a clear surface condition, and the inception of ice formation on surface 5. If there is water on top surface 5 of block 3, the voltage on the collector of transistor Q1 is around 5 volts, and the outputs of trigger circuits 77 and 85 are positive. The voltage on the collector of transistor Q1 causes single inputs of three NAND gates of logic circuit 87, designated by the reference characters G1, G3 and G5, to become High. (NOTE: Logic circuit 87 is implemented with TTL components, so in accordance with convention a High input or output is approximately +5 volts and a Low input or output is approximately 0 volts.) The other input to NAND gate G1 when only water is on surface 5 is a High supplied via line L17 from trigger circuit 85. The signal from trigger circuit 85 is limited to zero volts minimum by a diode D5 connected between ground and line L17 and to 5 volts maximum by a diode D7 connected between line L17 and a 5 volt source V17. The resulting low output of gate G1 is supplied to an inverter 89 which thereupon supplies a High output to a latch 91. The output of latch 91 thereafter becomes High and this High output is supplied to an output terminal T1, which High signal indicates the presence of water on pathway 6. Lamps, horns, etc., are connected to terminal T1 to provide a visual and/or audible indication of the presence of water on pathway 6.

As can be seen from the foregoing description, NAND gate G1 constitutes means responsive to the output signal from precipitation signal circuit 21 and to the output signal of state indicator circuit 49 failing to reach the predetermined alert threshold magnitude to provide an output at terminal T1 which indicates a wet surface condition.

The input to logic circuit 87 from ice indicator circuit 73, which is supplied to logic circuit 87 on line L15, is prevented by a clamping diode D9 connected to line L15 and a five-volt source V19 from exceeding 5 volts and is prevented by a clamping diode D11 connected to line L15 and ground from falling below zero volts. If there is ice on pathway 6, the output of ice indicator circuit 73 will be negative and the input to logic circuit 87 will be Low. This Low input is supplied to an inverter 93 which supplies its resulting High output to NAND gate G5. The other input to gate G5 will also be High since there is precipitation on pathway 6. The Low output of gate G5 is inverted by an inverter 95 and supplied to a latch 97 whose output becomes High as a result. This High output is supplied to a NOR gate G7, causing its output to be Low. This Low output is inverted by an inverter 99 and supplied to an output terminal T2 to indicate an icy surface condition. To summarize, electrical logic circuit 87 is responsive to the output signal from the precipitation signal circuit 23 and to the output signal from state indicator circuit 49 reaching the predetermined ice threshold magnitude to provide an output at terminal T2 which indicates an icy surface condition on pathway 6.

When there is a mixture of ice and water on pathway 6, the input to logic circuit 87 on line L15 is High and the input on line L17 is Low. The High input on line L15 is supplied to one input of gate G3, the other input of which is also High when precipitation is on pathway 6. The resulting Low output of gate G3 is inverted by an inverter 101 and the High output of inverter 101 is supplied to a NAND gate G9. The Low on line L17 is inverted by an inverter 103 and the resulting High outpt is supplied to the other input of gate G9, causing its output to be Low. Notice that if only ice were on pathway 6, the input to gate G9 from inverter 103 would still be High but the input from gate G3 and inverter 101 would be Low, causing the output of gate G9 to be High. That is, the output of gate G9 will be Low only when the predetermined alert threshold magnitude has been reached but the predetermined ice threshold magnitude has not been reached.

The Low output of gate G9 is inverted by an inverter 105 and the resulting High is supplied to a latch 107, resulting in its output being High. The High output of latch 107 is supplied to an inverter 109 and to an Exclusive OR gate G11. The other input to gate G11 is the output of latch 97, which is Low when there is a mixture of ice and water on pathway 6. The High output of gate G11 is supplied to another Exclusive OR gate G13. The other input of gate G13 is the output of latch 91, which is Low when there is any ice present on the top of block 3. The output of gate G13, accordingly, is High, which is supplied to a third Exclusive OR gate G15, the other input of which is connected to a five-volt source V21. The output of gate G15, therefore, is a Low which is supplied to a NOR gate G17. The other input to gate G17 is the output of gate G7, which is Low when there is a mixture of ice and water on the pathway. The resulting High output of gate G17 is supplied to a NOR gate G17, the other input of which is the Low output of inverter 109. The output of gate G19 is therefore High, which is supplied to a terminal T3 which indicates the inception of the formation of ice on top surface 5 of block 3.

If the output of state indicator circuit 49 is above the ice threshold magnitude, the inputs to logic circuit 87 on lines L15 and L17 are both Low, since the alert threshold magnitude is less than the ice threshold magnitude. If both those inputs are Low, gates G3 and G9 cause a Low to be present at the alert terminal T3. On the other hand, if only the signal on line L17 is Low, gates G3 and G9 cause a High to appear at terminal T3. Thus, gates G3 and G9 constitute means responsive to the output signal from precipitation signal circuit 23 (since one input to gate G3 is derived from that signal) and to the output signal of state indicator circuit 49 reaching the predetermined alert threshold magnitude but failing to reach the ice threshold magnitude to provide an output at terminal T3 which indicates the inception of the formation of ice on surface 5 of block 3.

At some point during the melting of the ice on pathway 6, the signal from state indicator circuit 49 will fall below the ice threshold magnitude. The surface of pathway 6 will still be in an extremely hazardous state, however, until all the ice has melted. To provide adequate warning of this hazardous state, a circuit, indicated generally at 111, consisting of gates G7, G11, G13, G15 and G17, maintains the voltage at terminal T2 High, thereby indicating an icy surface condition, until all the ice on pathway 6 has melted, i.e., until the signal from circuit 49 drops below the ice threshold and the alert threshold as well.

It is also desirable to provide an output signal which indicates a clear surface condition. By definition, there is a clear surface condition when there is an absence of precipitation on pathway 6. This is indicated by a Low on the collector of transistor Q1, i.e., the absence of an output signal from precipitation signal circuit 23. This Low, supplied to NAND gates G1, G3 and G5, causes the voltage at all three terminals, T1-T3, to be Low. Terminals T1-T3 are connected to a NOR gate G21. When pathway 6 is clear the resulting Lows supplied to the inputs of gate G21 from terminals T1-T3 cause the gate's output to be High. This High output is supplied to a fourth terminal T4, thereby indicating a clear surface condition. Clearly NOR gate G21 constitutes means responsive to the absence of the output signal from precipitation signal circuit 23 to provide an output at terminal T4 which indicates a clear surface condition.

Passing vehicles sometimes temporarily remove the precipitation from surface 5 of block 3. To prevent this temporary condition from causing a change at the indicator terminals T1-T3, sensor 1 includes a delay circuit, indicated generally at 113, which provides for a one-minute delay before the outputs of latches 91, 97 and 107 change.

In view of the above, it will be seen that the several objects of the invention are achieved and other advantageous results attained.

As various changes could be made in the above products without departing from the scope of the invention, it is intended that all matter contained in the above description or shown in the accompanying drawings shall be interpreted as illustrative and not in a limiting sense.

What is claimed is:

1. Apparatus for detecting wet and icy conditions on the surface of a pathway comprising:

a block of electrically insulative material adapted to be embedded in the pathway with the top surface of the block being substantially flush with the surface of the pathway and exposed to atmospheric precipitation;

a sensor electrode encapsulated in said block and positioned a predetermined distance beneath the top surface of the block so that the accumulation of atmospheric precipitation on said top surface affects the capacitance and conductance between said electrode and said pathway;

means for supplying to said sensor electrode a time-varying electrical current having an amplitude which is substantially constant and is independent of the accumulation of atmospheric precipitation on the top surface of said block;

an amplifier for amplifying an electrical signal applied to a pair of input terminals thereof;

means for commonly connecting one input terminal of said amplifier, the time-varying electrical current supplying means, and said pathway in the vicinity of the sensor electrode; means for connecting the sensor electrode to the other input terminal of said amplifier to complete a circuit between the time-varying electrical current supplying means, the sensor electrode and the amplifier thereby to apply an electrical signal to said amplifier, the amplitude of said signal at the input terminals of said amplifier being substantially solely a function of the change in capacitance and conductance between said sensor electrode and said pathway as atmospheric precipitation accumulates on the top surface of said block; and precipitation signal means responsive to the amplitude of an amplified electrical signal from said amplifier reaching a predetermined magnitude for providing an output signal indicative of the presence of atmospheric precipitation on the pathway.

2. Apparatus as set forth in claim 1 wherein the electrically insulative material comprises a thermosetting synthetic resin material.

3. Apparatus as set forth in claim 2 wherein the electrically insulative material further includes an inert filler material.

4. Apparatus as set forth in claim 3 in which the filler material has a dielectric constant substantially equal to that of the synthetic resin material.

5. Apparatus as set forth in claim 1 wherein the predetermined distance beneath the top surface of said block at which the electrode is positioned is on the order of one-quarter inch.

6. Apparatus as set forth in claim 5 wherein the sensor electrode is positioned on the top surface of a substrate material encapsulated in said block.

7. Apparatus as set forth in claim 1 wherein the means for supplying said time-varying electrical current includes an oscillator producing a sine wave at a frequency of approximately 5 KHz.

8. Apparatus as set forth in claim 1 wherein the precipitation means includes means for producing an electrical signal indicative of the presence of atmospheric precipitation on the pathway responsive to the amplitude of the amplified electrical signal falling to the predetermined magnitude.

9. Apparatus as set forth in claim 1 further including a second electrode, having a portion thereof exposed to the atmosphere, and means for commonly connecting it and the pathway thereby to enhance the electrical connection between the pathway and atmospheric precipitation on the top surface of the sensor block.

10. Apparatus as set forth in claim 1 further including a further electrode encapsulated in said block and connected to the pathway, said further electrode being spaced from the sensor electrode.

11. Apparatus as set forth in claim 10 wherein the sensor electrode and the further electrode are coplanar, said further electrode substantially surrounding said sensor electrode in their mutual plane.

12. Apparatus as set forth in claim 10 further including a second electrode, having a portion thereof exposed to the atmosphere, and means for commonly connecting it and the further electrode thereby to enhance an electrical connection between the pathway and atmospheric precipitation on the top surface of the sensor block.

13. Apparatus as set forth in claim 1 further including means connected to the electrical current means and the sensor electrode for compensating for temperature-induced changes in the dielectric constant of the insulative material making up said block.

14. Apparatus as set forth in claim 1 further comprising a pair of spaced electrodes exposed to atmospheric precipitation thereby to affect the resistance between said electrodes, said resistance being greater in the presence of ice than of water, state indicator means for supplying an output signal the magnitude of which is a function of the resistance between said pair of electrodes, said state indicator means being connected to said pair of electrodes, and an electrical logic circuit responsive to the output signal from the precipitation signal means and to the output signal from the state indicator means reaching a predetermined ice threshold magnitude to provide an output which indicates an icy surface condition.

15. Apparatus as set forth in claim 14 wherein said logic circuit includes means responsive to the output signal from the precipitation signal means and to the state indicator means output signal failing to reach a predetermined alert threshold magnitude to provide a second output which indicates a wet surface condition.

16. Apparatus as set forth in claim 15 wherein said logic circuit further includes means responsive to the absence of the output signal from the precipitation signal means to provide a third output which indicates a clear surface condition.

17. Apparatus as set forth in claim 16 wherein said logic circuit includes means responsive to the output signal from the precipitation signal means and to the state indicator means output signal reaching the predetermined alert threshold magnitude but failing to reach said ice threshold magnitude, the signal at the alert threshold magnitude corresponding to the resistance of said pair of electrodes with a mixture of ice and water on said surface, to provide a fourth output which indicates the inception of the formation of ice on said surface.

* * * * *